United States Patent [19]

Payne

[11] Patent Number: 4,579,690
[45] Date of Patent: Apr. 1, 1986

[54] PROCESS FOR THE DEOILING OF OLEFIN SULFONATES

[75] Inventor: Larry W. Payne, Houston, Tex.

[73] Assignee: Shell Oil Company, Houston, Tex.

[21] Appl. No.: 687,108

[22] Filed: Dec. 28, 1984

[51] Int. Cl.$^4$ ............................................. C07B 13/00
[52] U.S. Cl. .......................... 260/504 S; 260/504 R; 260/513 R; 260/513 T
[58] Field of Search ............ 260/504 S, 504 R, 513 T, 260/513 R

[56] References Cited

U.S. PATENT DOCUMENTS

| | | | |
|---|---|---|---|
| 2,781,315 | 2/1957 | Bray | 260/504 R |
| 3,888,917 | 6/1975 | Fendress et al. | 260/504 R |
| 4,321,216 | 3/1982 | Delgado | 260/504 S |

Primary Examiner—Alan Siegel

[57] ABSTRACT

An improved process for the solvent extraction of free oil from $C_8$ to $C_{24}$ olefin sulfonation products, which comprises steps for contacting an olefin sulfonation product containing free oil with an alkane-based extraction solvent and phase separating the resulting mixture into an extract phase enriched in free oil and a raffinate phase enriched in sulfonated matter. The invention is particularly directed to the use in such a process of an extraction solvent which comprises one or more $C_4$ to $C_9$ alkanes and between about 5 and 35 percent by weight of dimethyl ketone. Deoiled sulfonation products are known for utility as components of detergent formulations for industrial, household and personal care uses.

20 Claims, No Drawings

4,579,690

PROCESS FOR THE DEOILING OF OLEFIN SULFONATES

BACKGROUND OF THE INVENTION

The present invention relates to an improved extraction process for the deoiling of the products of the sulfonation of higher olefins. More particularly, the invention relates to improvements in such a process which are associated with the use of an alkane-based extraction solvent comprising a particular cosolvent.

It is well known to prepare valuable anionic surfactants by the sulfonation reaction between detergent range (e.g., $C_8$ to $C_{24}$) olefins and sulfonating agents such as sulfur trioxide. Olefin sulfonate products have found commercial utility in detergent formulations for industrial, household and personal care uses. Interest has recently been shown in their application in enhanced oil recovery processes.

In essentially all cases, the olefin sulfonation reaction does not accomplish complete conversion to the desired surface active sulfonate compounds (referred to as active matter), and the crude product contains a significant amount (e.g., 3 to 30%) of the unsulfonated olefin starting material (referred to as fee oil or neutral oil). Free oil represents a particularly objectionable impurity in the sulfonation product, from the standpoint of its influence upon detergency, foaming, color, odor and other physical and chemical properties.

Various processes have been proposed in the art to remove free oil from (i.e., to "deoil") olefin sulfonates and related anionic organic surfactants, both to improve product quality and to recover valuable olefin for recycle to the sulfonation reaction. As a general rule, such processes involve extraction of the free oil, using an extraction solvent which is based upon an alkane and which additionally contains a lesser amount of a cosolvent. Clear preference has been expressed in the prior art for a cosolvent which is a lower alkanol, most particularly isopropyl alcohol. For example, U.S. Pat. No. 4,322,367 describes processes for the extraction of oils from sulfates and other anionic detergents, using an extraction solvent which comprises both a $C_4$ to $C_g$ hydrocarbon, most preferably hexane, and a $C_1$ to $C_3$ alcohol, most preferably isopropanol. According to that patent, related processes involving extraction systems containing hydrocarbon and/or alcohol solvents are described in U.S. Pat. No. 2,412,916, U.S. Pat. No. 2,655,530, U.S. Pat. No. 2,673,207, U.S. Pat. No. 2,687,420, and U.S. Pat. No. 3,941,810. It has also been found that U.S. Pat. No. 2,820,056, U.S. Pat. No. 3,444,191, U.S. Pat. No. 3,496,226, U.S. Pat. No, 3,842,095, U.S. Pat. No. 3,862,983, U.S. Pat. No. 4,197,255, and U.S. Pat. No. 4,318,823 each reports an extraction of an organic sulfonation product which involves a $C_4$ to $C_9$ alkane and/or a lower, water soluble alcohol solvent. U.S. Pat. No. 4,248,793 describes a similar extraction process employing a halogenated hydrocarbon solvent. U.S. Pat. No. 4,321,216 teaches a mixed deoiling extraction solvent comprising immiscible polar (e.g., carboxylic acid) and nonpolar (e.g., octane) components.

It is also common practice in the art to conduct analyses of the free or neutral oil content in organic sulfonation products by extraction with alkane and/or alcohol solvents. The publication by F. T. Weiss, A. E. O'Donnell, R. J. Shreve and E. D. Peters entitled "Comprehensive Analysis of Sodium Alkyl Aryl Sulfonate Detergents" "Analytical Chemistry, Vol. 27, No. 2, Feb. 1955, pp. 198–205) describes a separation of neutral oil from alkyl aryl sulfonates by extractions with petroleum ether (pentane) and isopropyl alcohol. ASTM Method D-3673 is directed to similar analytical procedures.

Although extraction processes utilizing alkane-based solvents containing alcohol cosolvents are recognized to be effective for the deoiling of organic sulfonates, they are typically not as efficient as would be desirable in this service. In general, conventional deoiling practices necessarily make use of relatively large quantities of solvent and/or of multiple extraction stages to reduce free oil content to the extent desired. It is the principal object of this invention to provide a process having improved efficiency for the deoiling of olefin sulfonates.

In one important respect, the present invention is directed to discoveries associated with the use of dimethyl ketone (acetone) as a cosolvent in an alkane-based solvent extraction process for the deoiling of olefin sulfonates.

In this regard, the prior art teaches only that under certain conditions, sulfonation products are soluble in acetone, alcohols, water, and the like. U.S. Pat. No. 2,243,332 discloses that sulfonation products may be applied (for instance, as detergents, emulsifiers, textile treating agents, tanning agents, mineral flotation agents, etc.) in the form of solutions in water, alcohol or acetone. U.S. Pat. No. 2,673,208 describes the extraction of an organic sulfonate from a mixture containing inorganic salts, which comprises treating the mixture with an organic solvent such as a lower alcohol, a fatty acid glycol ester, a ketone (including acetone, methylethyl ketone, diethyl ketone and their substituted derivatives) isobutyric acid, dioxane, and various ethers. U.S. Pat. No. 3,644,499 discloses a process for producing detergent sulfonates by reaction of an olefinic compound with an alkali bisulfate sulfonating agent, necessarily carried out in the presence of a reaction solvent containing both a polar solvent and an organic solvent such as a lower alcohol, a ketone such as acetone, methylethyl ketone, diethyl ketone, and diisobutyl ketone, tetrahydrofuran, and dimethylformamide. On the other hand, the examples of U.S. Pat. No. 3,487,104 describe a process for converting a sultone to an alkene sulfonate, wherein the product is purified by recrystallizations from methanol and washings with hot methyl ethyl ketone and dimethyl ketone, indicating that the sulfonate is soluble in methanol but not in the lower ketones.

SUMMARY OF THE INVENTION

The present invention provides an improvement in processes for the solvent extraction of free oil from olefin sulfonation products. This improvement centers upon a particular extraction cosolvent combination of a $C_4$ to $C_9$ alkane with dimethyl ketone and the discovery that such solvent offers enhanced extraction efficiency relative to the performance of hydrocarbon and alcohol solvent combinations preferred in the prior art.

Accordingly, the present invention is briefly described as an improvement in a solvent extraction process which comprises steps for contacting an olefin sulfonation product containing free oil with an alkane-based extraction solvent and phase separating the resulting contact mixture into an extract phase enriched in the free oil and a raffinate phase enriched in sulfonated matter, said improvement comprising the use in the contact step of an alkane-based extraction solvent which comprises one or more $C_4$ to $C_9$ alkanes and between about 5 and 35 percent by weight of dimethyl ketone, calculated on total weight of the alkanes and the dimethyl ketone.

DESCRIPTION OF THE PREFERRED EMBODIMENTS

The present invention is broadly applicable to the treatment of products of the sulfonation of detergent range olefins which contain unconverted olefin starting material.

It is most common in the art to describe olefin sulfonation products in terms of the one or more olefins (i.e., alkenes) from which they are prepared. For purposes of the present invention, these olefins have a carbon number in the range from about 8 to 24. Primarily from the standpoint of the utility and value of the product, the olefins have a carbon number which is preferably in the range from about 10 to 22 and more preferably in the range from about 11 to 20.

In terms of molecular structure, the olefins of interest may be either linear (straight-chain) or branched, although again preference may exist for linear olefins from the standpoint of product value. Double bond position in the olefin molecule is likewise not a critical aspect in describing such olefins, and the invention is very suitably applied to sulfonation products derived from either alpha or internal olefins. As a general rule, there is typically a greater need for deoiling of the sulfonation products of internal olefins and greater benefits to be realized in this case from enhanced efficiency of the invention. Sulfonation processes involving predominantly internal olefins are characterized by a low conversion of olefin, in comparison to reactions of corresponding alpha-olefins, and the internal olefin sulfonation products thus contain comparatively higher quantities of free oil.

As specific examples of detergent range olefins useful in the preparation of sulfonation products to which the present invention may be usefully applied, mention may be made of mixtures of olefins prepared according to a variety of known methods and available from a number of commercial sources. For instance, olefin mixtures having a relatively high linear alpha-olefin content are manufactured by the cracking of paraffin wax and by the oligomerization of ethylene using Ziegler catalysts. Higher linear alpha-olefin mixtures are manufactured, generally according to the disclosures of U.S. Pat. Nos. 3,676,523, 3,686,351, 3,737,475, 3,825,615 and 4,020,121, and sold under the NEODENE trademark by Shell Chemical Company. Internal olefins in the $C_8$ to $C_{24}$ range are produced by the chlorination-dehydrochlorination of paraffins, by paraffin dehydrogenation, and by the isomerization of alpha-olefins.

Conversion of such olefins to the sulfonation products of interest typically involves both a reaction with sulfur trioxide and subsequent neutralization and/or hydrolysis of the $SO_3$ reaction mixture. The term "sulfur trioxide" as used herin is intended to include any compound or complex which contains or yields $SO_3$ as a sulfonation reactant, as well as $SO_3$ per se. Methods are well known in the art for conducting olefin sulfonation reactions and typically involve contact of a flow of dilute $SO_3$ vapor with a thin film of liquid olefins at a temperature in the range of about 40° F. to 120° F. The reaction between the $SO_3$ and the olefins yields a mixture containing both sulfonic acids and sultones. In conventional practice, this mixture is then typically subjected to hydrolysis under alkaline conditions, e.g., in the presence of an alkali or alkaline earth metal or ammonium hydroxide or carbonate, which accomplishes both a hydrolysis of the sultones to sulfonic acids and a neutralization of the sulfonic acids to sulfonic acid salts (sulfonates). The invention is applicable not only to the hydrolyzed and neutralized sulfonation products resulting from such alkaline hydrolysis, but also to those sulfonation products in the form of the sulfonic acids such as result from the hydrolysis of the $SO_3$ reaction product under acidic conditions. Procedures for hydrolysis of $SO_3$ reaction products, with or without neutralization, are well known in the prior art. It is further possible, although not preferable to apply the invention to the unhydrolyzed $SO_3$ reaction mixture containing sultones at the expense, however, of the extraction of a portion of the sultones with the neutral oil. Most preferably, the invention is utilized to deoil the hydrolyzed and neutralized sulfonate products. Such products, it will be understood, are a complex mixture of compounds principally comprising alkene sulfonic acid salts, hydroxyalkane sulfonic acid salts and alkene disulfonic acid salts. Although the composition of the sulfonate product varies somewhat depending upon a number of factors, particularly the nature of the olefin and the $SO_3$ reaction conditions, these three principle components would typically be present in the product in quantities of about 50 to 70% by weight (%w), 20 to 40%w, and 5 to 15%w, respectively, of the total surface-active content (or active matter content) of the product. Other substances which commonly contribute, in lesser amount, to the products's active matter, are the higher order alkene sulfonates and hydroxy-alkane sulfonates. Non-active matter components include the free oil, water, and inorganic salts.

For purposes related to product stability and handling, olefin sulfonates are typically prepared as solutions in water. The invention is suitably and preferably applied to the deoiling of sulfonation products which contain water, more preferably to products which contain at least about 50%w water and most preferably to products which contain at least about 60%w water.

The invention necessarily comprises a contact step, in which the free oil containing sulfonation product is intimately mixed with the alkane/dimethyl ketone extraction solvent, and a phase separation step in which the resulting contact mixture is settled and physically separated into an (upper) extract phase, enriched in the free oil, and a (lower) raffinate phase, enriched in sulfonated matter.

In essence, the invention centers upon discoveries concerning an extraction solvent for the deoiling of olefin sulfonate products, which is necessarily based upon one or more $C_4$ to $C_9$ alkanes and also contains a lesser amount of dimethyl ketone. The dimethyl ketone (DMK) cosolvent has been found to be of critical importance to the performance of the invention. As a component for alkane-based deoiling solvents, DMK offers meaningful improvement in extraction performance, relative to either the alkanes alone or to the alkane/isopropyl alcohol solvent combination preferred by the prior art. Moreover, this improvement is specific to the use of DMK. Other ketones most closely related to DMK, for instance methylethyl ketone and diethyl ketone, do not offer suitable performance as cosolvents for alkane-based extraction solvents when used in the deoiling of olefin sulfonation products.

For purposes of the invention, the alkane(s) are the major component of the extraction solvent and, in particular, are present in an excess by weight over the DMK. Preference exists for an extraction solvent which contains between about 5 and 35 percent by weight (%w) DMK, calculated on the weight of the $C_4$ to $C_9$ alkanes. A proportion of DMK between about 8 and 30%w, calculated on alkanes, is more preferred, while a proportion between about 12 and 24%w, calculated on alkanes is generally considered most preferred.

Of the alkanes suitable for use in the extraction solvent, preference can usually be expressed for a solvent in which the major fraction of the alkane component is in the $c_5$ to $C_8$ range, while one in which a major fraction is in the $C_6$ to $C_8$ range is more preferred. $C_4$ and in some cases lower alkanes are suitable for inclusion in the solvent, although their use may require that the process be operated under pressure. $C_9$ and in some cases higher alkanes are suitable but are not as readily recovered (e.g., by evaporation) from extract and raffinate products.

In the contact step, the solvent is intimately mixed with the sulfonation product. Relative quantities of solvent and sulfonation product are not critical, and a broad range of proportions (e.g., from about 10 parts solvent to one part sulfonation product to about 10 parts sulfonation product to one part solvent) are considered useful. Solvent is preferably applied in a quantity (by weight) which is between about 1 and 8 times, more preferably between about 1 and 6 times, that of the total sulfonation product mixture. Taking into account the most common and preferred practice in which the sulfonate product contains between about 50 and 80%w water, preference is then typically exists for a quantity of solvent which is about 1 to 30 times by weight that of the active matter and particularly for a quantity of solvent which is about 2 to 20 times that of the active matter. As will be understood to those familiar with the extraction art, the optimal quantities of solvent relative to sulfonation product for a given process application will depend upon the product's relative quantities of water, active matter, and free oil, as well as upon the desired degree of free-oil extraction.

Alkane and DMK can be added to the contact step mixture either as a combination, or independently in any order. Practice under the invention has not been observed to give rise to any problems, as encountered for some alkane-based solvents in the prior art, of the formation of emulsions and gels in the extraction mixture.

Apart from considerations regarding the alkane and DMK extraction solvent mixture, the process of the invention may suitably be carried out using equipment and procedures known in the art for extraction of free oil from sulfonation products with alkane-based solvents. Illustrations of suitable practices are provided by the aforementioned patents describing deoiling extractions with alkane and alcohol solvents, the relevant disclosures of which are incorporated herein by this reference.

In general, each of the process steps may be carried out in either a batch, semi-continuous, or continuous manner, although continuous operation is typically preferred. Both single stage and multistage extractions are very suitable under the invention. Process temperatures for both the contact and the phase separation steps are preferably in the range from about 0° to 100° C., while temperatures in the range from about 10° to 80° C. are more preferred and those in the range from about 20 to 60° C. are considered most preferred. Process pressure is not a critical factor and it is only necessary to operate at a pressure which maintains solvent in the liquid phase. Pressures in the range from 0 to 50 psig are typical, but not limiting. Higher pressures may be necessary if the contact mixture contains a relatively large proportion of either DMK or the lower (e.g., $C_4$ and $C_5$) alkanes.

In the phase separation step of the invention, the mixture resulting from the contact step is settled and physically separated into two distinct liquid phases—an upper extract phase containing solvent and enriched in free oil (relative to the total contact mixture) and a lower raffinate phase containing solvent and enriched in active matter (relative to the total contact mixture). Water is present substantially in the raffinate phase. As a general rule, the contact mixture settles by gravity relatively rapidly into the two phases, without the need for centrifugation, chilling, application of electrostatic fields or the like, although such conventional aids to phase separation may be suitably employed.

Following the phase separation step, it is typically desirable to treat both the extract and the raffinate to recover extraction solvent. As in prior art practice with alkane-based extraction solvents, solvent recovery is very conveniently accomplished by evaporation or distillation of the extract and raffinate.

In usual practice, the invention has the advantage of removing other impurities as well as free oil from the sulfonation product, including both those which may be introduced into the sulfonation product with the olefin feedstock (e.g., detergent range alkanes) and are not converted to surface active matter, as well as those which may be formed as by-products in the sulfonation process (e.g., color bodies and olefin dimers).

The invention is further illustrated by reference to the following Examples, according to the invention, and Comparative Experiments, not according to the invention. The Examples are provided to illustrate certain specific embodiments of the invention and are not intended to limit its broader scope.

EXAMPLE 1

A process according to the invention was applied to the deoiling of an aqueous "feedstock" mixture, the sodium salts of the sulfonation product containing of $C_{17}$-$C_{20}$ internal olefins in a concentration of sulfonated matter of about 33%w. This mixture contained about 17.5%w oil, calculated on active matter Initially, 40 g of the feedstock mixture and 119 g of n-heptane were added to a 250 ml separatory funnel. Dimethyl ketone (25ml, 20g) was then added and the mixture shaken. Overall, the funnel contained 139g of solvent (16.8% DMK calculated on heptane) for a solvent to feedstock weight ration of 3.45:1 and a solvent to active matter weight ration of 10.5:1. The mixture rapidly settled (with settling complete in 3 minutes) into two phases, which were then separated. The bottom raffinate phase was analyzed and found to contain only 3.7%w oil, calculated on active matter, representing a 79% removal of oil in the single extraction step.

COMPARATIVE EXPERIMENT

An experiment was carried out, not in accordance with the invention, utilizing an extraction solvent containing heptane and isopropyl alcohol (16.8%w isopropyl alcohol calculated on heptane). Otherwise, the same procedures as described for Example 1 were followed for the deoiling of the same feedstock. The solvent (139 g total—119g heptane and 20 g isopropanol) was again mixed with the aqueous suflonate feedstock (40 g) in an overall weight ratio of 3.45:1 and in a solvent to active matter ratio of 10.5:1. Separation of the resulting liquid phases resulted in a raffinate containing 5.8%w oil calculated on active matter, representing a deoiling efficiency of only 67%.

COMPARATIVE EXAMPLE B

Attempts were made to extract oil from the sulfonate feedstock employing heptane as the sole extraction solvent. Phase separations were slow and analyses indicated that there was essentially no removal of oil from the raffinate phase.

COMPARATIVE EXAMPLE C

For comparative purposes, an experiment was carried out, not in accordance with the invention, utilizing an extraction solvent containing methylethylketone (MEK) and heptane. An extraction mixture of 20 g of the aqueous $C_{17}$-$C_{20}$ sulfonate mixture and 65 g of a solvent containing 4 g MEK and 61 g heptane formed a viscous emulsion, failed to phase separate over 30 minutes.

Addition of a further 4 g of MEK gave a total of 69 g of a solvent containing 13.1%w MEK calculated on heptane, an overall solvent to feedstock weight ratio of 3.25:1 and a solvent to active matter weight ratio of 9.9:1. From the resulting extraction mixture, two phases separated in about one hour. Raffinate was analyzed and found to contain 10.1%w oil, representing an oil removal of only 42%.

EXAMPLE 2

A process according to the invention was applied to a two-stage deoiling extraction. The first stage of this process was carried out, as described in Example 1, for the treatment of an olefin sulfonate feedstock containing 17.5%w oil to reduce its oil content to 3.7%w. In a second extraction stage, the raffinate from the first stage was mixed with solvent (heptane and DMK, with 16.8%w DMK calculated on heptane) in a solvent to first stage raffinate (second stage feed) of 1.52:1 by weight and in a solvent to active matter ratio of 8.0 to 1 by weight. The resulting second stage extraction mixture was allowed to settle and the two resulting phases separated. The second stage raffinate was analyzed and determined to contain only 1.1% oil. Overall, extraction efficiency for this two-stage process was 94%.

I claim as my invention:

1. In a process for the separation of free oil from an olefin sulfonation product containing free oil, which comprises steps for contacting the sulfonation product of one or more $C_8$ to $C_{24}$ olefins with an alkane-based extraction solvent and phase separating the resulting contact mixture into a liquid extract enriched in free oil and a liquid raffinate enriched in sulfonated matter, the improvement comprising the use as the extraction solvent of an alkane-based solvent which comprises one or more $C_4$ to $C_9$ alkanes and between about 5 and 35 percent by weight of dimethyl ketone, calculated on total weight of the alkanes and dimethyl ketone.

2. The process of claim 1, wherein the process is carried out in the temperature range from about 0° to 100° C.

3. The process of claim 2, wherein the alkane-based solvent contains between about 8 and 30 percent by weight of dimethyl ketone, calculated on total weight of the alkanes and the dimethyl ketone.

4. The process of claim 3, wherein the sulfonation product is a sulfonation product prepared by sulfonation, hydrolysis and neutralization of one or more olefins having a carbon number in the range from about 10 to 22, and contains at least about 50 percent by weight water.

5. The process of claim 3, wherein a major fraction of the alkane component of the extraction solvent is in the $C_5$ to $C_8$ range.

6. The process of claim 5, wherein the process is carried out in the temperature range from about 20° and 60° C.

7. The process of claim 1, wherein the quantity of extraction solvent in the contact mixture is about 2 to 20 times that of the sulfonation product.

8. The process of claim 7, wherein the process is carried out in the temperature range from about 0° to 100° C.

9. The process of claim 8, wherein the alkane-based solvent contains between about 8 and 30 percent by weight of dimethyl ketone, calculated on total weight of the alkanes and the dimethyl ketone.

10. The process of claim 9, wherein the sulfonation product is a sulfonation product prepared by sulfonation, hydrolysis and neutralization of one or more olefins having a carbon number in the range from about 10 to 22, and contains at least about 50 percent by weight water.

11. The process of claim 10, wherein a major fraction of the alkane component of the extraction solvent is in the $C_5$ to $C_8$ range.

12. The process of claim 11, wherein the process is carried out in the temperature range from about 20° to 60° C.

13. The process of claim 8, wherein the sulfonation product contains at least about 60 percent by weight water.

14. The process of claim 10, wherein the sulfonation product contains at least about 60 percent by weight water.

15. The process of claim 12, wherein the sulfonation product contains at least about 60 percent by weight water.

16. The process of claim 15, wherein the alkane-based solvent contains between about 12 and 24 percent by weight of dimethyl ketone, calculated on total weight of the alkanes and the dimethyl ketone.

17. The process of claim 16, wherein the sulfonation product is prepared from predominantly internal olefins.

18. In a process for the separation of free oil from an olefin sulfonation product containing free oil, which comprises steps for contacting the product of sulfonation, hydrolysis and neutralization of one or more $C_{11}$ to $C_{20}$ olefins with an alkane-based extraction solvent and phase separating the resulting contact mixture into a liquid extract enriched in free oil and a liquid raffinate enriched in sulfonated matter, the improvement comprising the use as the extraction solvent of a solvent which is based on one or more $C_6$ to $C_8$ alkanes and which additionally comprises between about 12 and 24 percent by weight of dimethyl ketone, calculated on total weight of the alkanes and the dimethyl ketone.

19. The process of claim 18, wherein the sulfonation product contains at least about 60 percent by weight water.

20. The process of claim 19, wherein the process is carried out in the temperature range from about 20° to 60° C.

* * * * *